ary Examiner—Natalie Trousof
Attorney, Agent, or Firm—William H. Edgerton

United States Patent [19]
Gyurik et al.

[11] 3,969,526
[45] July 13, 1976

[54] ANTHELMINTIC 5-HETEROCYCLIOTHIO AND OXY-2-CARBALKOXYAMINOBENZIMIDAZLES

[75] Inventors: Robert J. Gyurik, West Brandywine; William D. Kingsbury, West Chester, both of Pa.

[73] Assignee: SmithKline Corporation, Philadelphia, Pa.

[22] Filed: Dec. 9, 1974

[21] Appl. No.: 530,781

Related U.S. Application Data

[63] Continuation-in-part of Ser. No. 364,841, May 29, 1973, abandoned.

[52] U.S. Cl.................. 424/273; 260/250 R; 260/250 A; 260/256.4 R; 260/256.5 R; 260/294.8 C; 260/295 R; 260/306.8 R; 260/306.8 D; 260/307 R; 260/307 G; 260/308 R; 260/308 D; 260/309.2; 424/250; 424/251; 424/263; 424/269; 424/270; 424/272

[51] Int. Cl.$^2$............... C07D 405/12; C07D 409/12
[58] Field of Search................ 260/309.2; 424/273

[56] References Cited
UNITED STATES PATENTS

| | | | |
|---|---|---|---|
| 3,480,642 | 11/1969 | Stedman | 260/309.2 |
| 3,574,845 | 4/1971 | Actor et al. | 260/309.2 |
| 3,657,267 | 4/1972 | Van Gelder et al. | 260/309.2 |

FOREIGN PATENTS OR APPLICATIONS

| | | |
|---|---|---|
| 2,411,295 | 3/1974 | Germany |

*Primary Examiner*—Natalie Trousof
*Attorney, Agent, or Firm*—William H. Edgerton

[57] ABSTRACT

New methyl benzimidazolecarbamate compounds having a heterocyclic thio or oxy moiety at position 5, useful as anthelmintics are described. Methyl-5-(pyridylthio)- and 5-(pyridylmethylthio)-benzimidazolecarbamates are preferred.

11 Claims, No Drawings

ANTHELMINTIC 5-HETEROCYCLIOTHIO AND OXY-2-CARBALKOXYAMINOBENZIMIDAZLES

This application is a continuation-in-part of our co-pending application, Ser. No. 364,841, filed May 29, 1973, now abandoned.

This invention comprises a series of new substituted benzimidazoles whose structure is characterized by having a 5 to 6-membered ring, especially one containing a nitrogen member having basic properties, in the 5-position. These compounds have useful anthelmintic properties.

More specifically, the compounds of this invention are represented by the following structural formula:

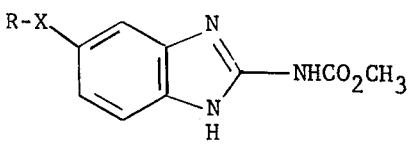

FORMULA I in which X is thio or oxy; and R is a 5 or 6-membered aromatic heterocyclic ring having at least one nitrogen, oxygen or sulfur member but not more than one oxygen or sulfur member and not more than four nitrogen members, such as pyridyl, furyl, thienyl, imidazolyl, oxadiazolyl, thiadiazolyl, pyrazinyl, tetrazolyl, pyridazyl, pyrimidyl, oxazolyl, thiazolyl, triazolyl or thiatriazolyl. Pyridyl is preferred.

The hetero ring may be attached to the oxy or thio atom through a C-ring member or through a lower alkylene chain of from 1–4 carbon atoms but the attachment is preferably through a methylene group. One skilled in the art will recognize that certain of the heterocyclic moieties mentioned may be limited in the unstability or unavailability of certain precursor compounds such as the mercaptans, hydroxy heterocyclics or the active halo-substituted heterocyclics. Those skilled in the art will recognize these problem areas readily. Reference may be made for example to page 166 of "The Principles of Heterocyclic Chemistry", Katritzky, Academic Press (1968). The following description and examples will clarify this invention.

Especially active are the compounds of Formula I in which X is thio. Of advantage are the compounds of Formula I in which R is pyridyl or pyridylmethyl, in particular those attached at the 2 or 4-positions of the pyridyl ring.

Also included in this invention are those compounds related to Formula I above in which trivial substituents are optionally present on the ring as known to the art, such as chloro, bromo, iodo, methyl, ethyl, cyano, nitro or carbomethoxy. Starting materials and methods of preparing them in the illustrative and preferred pyridyl series are disclosed in Chapter XV, pages 383–387 and 347–359 of part four of the fourteenth volume of "Heterocyclic Compounds", Klingsbery, Interscience (1964).

As far as we know, no lower alkyl 5-heterocyclic thio or oxy-2-carbalkoxyamino-benzimidazoles have been reported in the prior art before our invention. Lower alkylthio and oxy (U.S. Pat. No. 3,682,952), phenylthio and oxy (Belgian Pat. No. 793,358) and benzylthio (Belgian Pat. No. 809,234), (Derwent No. 58670V/33, 53171V/29) congeners have been reported as anthelmintics.

Included in this invention are derivatives of the compounds of Formula I which contain basic centers especially the preferred pyridyl derivatives such as nontoxic, pharmaceutically acceptable salts prepared from organic or inorganic acids as known to the pharmaceutical art, for example those formed with hydrochloric, hydrobromic, sulfuric, phosphoric, sulfamic, acetic, benzoic, malic, maleic, ethane sulfonic, fumaric, etc., acids. Also certain acyl or alkyl derivatives at the N-atoms in the benzimidazole ring can be optionally formed as known to the art. For example, the N'-acyl groups may be amido, lower alkyl amido, dilower alkyl amido, ω-dilower alkylaminoalkyl, lower alkanoyl such as acetyl or propionyl. They are prepared as known to the art, for example as in Belgian Pat. No. 809,235.

Also included where pertinent are the oxide derivatives of the compounds of Formula I such as the N-oxide derivatives of the pyridyl containing benzimidazoles. These are prepared using mild oxidizing agents, such as peracetic or perbenzoic acid. Also the oxide (—SO—) or dioxido (—SO$_2$—) derivatives of the compounds are prepared by mild oxidation, most preferably at the end product stage, for example, using either one equivalent (—SO—) or two equivalents (—SO$_2$—) of hydrogen peroxide and acetic acid.

The description of this invention is limited to representative compounds having novel modifications of structure at the 5-position which characterize this invention. Other carbamate esters may be substituted in the general invention as known to the art, for example lower alkyl of from 1-8 carbon atoms such as methyl, ethyl or propionyl, furyl, benzyl, etc. Other acyl groups may be substituted on the 2-amino, for example lower alkanoyl such as acetyl or propionyl, benzoyl, furoyl, etc. These give little advantage in activity or chemical cost over the methylcarbamyl congeners.

The compounds of this invention are prepared and used by methods described herein or similar to those described in U.S. Pat. No. 3,682,952 but using the known active halides, hydroxy or mercaptan compounds as starting materials for preparing the phenylenediamine intermediates. The preferable route of synthesis is the reaction of a 4-heterocyclic thio- or oxy-o-phenylenediamine with methyl cyanocarbamate, formed from cyanamide and methyl chloroformate. The formation of the benzimidazoles of Formula I usually is carried out by reacting the starting materials in a solvent in which they are at least partially soluble, preferably with heating such as at reflux or, after the solvent has been removed, at 50°–125°C. Most useful is an aqueous miscible solvent system in which the reactants are at least partially soluble in the presence of alkali, such as an alkali metal hydroxide or carbonate. The solvent systems most useful are acetone, methanol, ethanol, pyridine, dimethylsulfoxide, dimethylacetamide, dimethylformamide and the like. As noted the reaction is carried out at temperatures ranging from room temperature up to the boiling point of the reaction mixture or, if the solvent is high boiling, to steam temperature. The duration is usually from one-half to eight hours. The product is isolated by standard chemical methods.

The important 4-heterocyclic thio and oxy-o-phenylenediamine starting materials may be alternatively prepared by two alternative reactions. A reactive 5-halo-2-nitro acetanilide is reacted with a known reactive heterocyclic mercaptan or hydroxide. Altrnatively a reactive heterocyclic halide, usually the chloride or bromide, may be reacted with 3-amino-4-nitrophenol or thiol. The latter reaction is, of course, very useful either to prepare the preferred methylene compounds using known heterocyclic methyl halides or using haloheterocyclics whose halo groups are reactive as are the 2 or 4-chloro or bromo atoms on the pyridine ring. Also the halo reaction is used to prepare starting materials of unreactive thiols or hydroxides.

The resulting 5-(heterocyclicthio or oxy)-2-nitroanilines are submitted to catalytic hydrogenation to give the phenylenediamine intermediates which are used in either the cyanamide or isothiourea process. Both of these groups of intermediates are part of this invention.

As an alternative those skilled in the art will recognize that in the heterocyclic starting materials, i.e., the thiol or hydroxyls the tautomeric forms of the heterocyclic hydroxy or thiol starting material may favor the keto or thione structure thereby making the described alkylation not practical. In these cases often the corresponding reactive haloheterocycle may be optionally condensed with 3-amino-4-nitrophenol or thiol to obtain the desired substituted phenylenediamine in the alternative reaction. The chloromethyl and bromomethylheterocyclic compounds are often easily prepared by standard halomethylation reactions.

The 5-heterocyclic thio- and oxybenzimidazoles of Formula I have useful anthelmintic properties, that is, broad spectrum activity against parasites of warm blooded host animals, including both mature and immature parasitic forms. In particular, these compounds have high activity against various helminthic infections of the intestinal tract of economically important animals, coupled with low systemic toxicity to the host animal. The most important animal hosts are horses, pigs, dogs and ruminant animals such as cattle or sheep.

For example, the disclosed compounds are generally effective in clearing mice of worm infections for laboratory purposes, among others: *Syphacia obvelata* and *Aspicularis tetraptera* (mouse pinworm), *Nematospiroides dubius* (mouse hookworm), and the migratory stages of *Ascaris suum*.

Other susceptible helminths include *Toxocara canis*, found in naturally infested dogs. Also, parasitic to this host are *Ancylostoma canium*, *Trichuris vulpis* (whipworm), and *Physalaptera spp.*

These compounds are efficacious against parasites of pigs, such as the migratory stages of *Ascaris suum*, thus preventing the development of verminous pneumonia.

Compounds of Formula I are most efficacious against parasitic gastroenteritis in sheep, such as *Haemonchus contortus*, *Ostertagia spp.*, *Trichostrongylus spp.*, *Nematodirus spp.*, *Trichuris ovis*, *Cooperia spp.*, and *Strongyloides papillosus*. *Bunostomum trigonocephalum* and *Oesophagostomum spp.*, are other important parasites of sheep.

Animals of low weight are treated with unit doses ranging no higher than a few milligrams; whereas animals of high body weight, such as ruminants, require proportionately larger unit doses ranging up to several grams. Preferably, a single dose is administered daily for each animal species based on the weight of that species.

The amount of ingredient administered will depend on the weight of the host, but will usually be between about 1 mg./kg. and 100 mg./kg. of body weight daily.

In nematode infections in sheep from about 1-25 mg./kg. of the 5-heterocyclicthio-2-carbomethoxyaminobenzimidazoles would be found effective in clearing substantially all the worms from the intestinal tract. Essentially the compounds of Formula I at a minimum have the same spectrum as parbendazole but the preferred compounds are more active, i.e., active at lower doses of active ingredient in many cases.

In practice, an active compound of the structure of Formula I is usually formulated with a nontoxic carrier therefor to give anthelmintic compositions of this invention. The carrier may be an orally ingestible container for the active ingredient, for example, a hard or soft gelatin capsule; or it may be a pharmaceutically acceptable diluent or excipient of the kind normally used in the production of medicaments, ready for use, for example maize starch, terra alba, lactose, sucrose, calcium phosphate, gelatin, talcum, stearic acid, magnesium stearate, dextrin, agar, pectic or acacia.

Exemplary of liquid carriers are peanut oil, olive oil, sesame oil, and water. Similarly, the carrier or diluent may include a time delay material such as glyceryl monostearate or glyceryl distearate alone or with a wax.

A wide variety of pharmaceutical forms can be employed. Thus, if a solid carrier is used, the preparation can be tableted, placed in a hard gelatin capsule, or compounded in the form of a troche or lozenge. The amount of solid carrier will vary widely but preferably will be from about 25 mg. to about 3 gm. If a liquid carrier is used, the preparation may be in the form of a soft gelatin capsule, placed in an ampule or in liquid suspension.

The compositions are most often made up in a form suitable for oral administration and may therefore take the form of a liquid, for example, an emulsion or a solution or suspension in water, oil, such as arachis oil, or other liquid.

The compositions are advantageously made up in a dosage unit form adapted for the desired mode of administration. Thus for the preferred oral administration, the dosage unit may take the form of a suspension, tablet, packaged powder, bolus, or encapsulated powder. The quantity of active ingredient in each dosage unit will be such that one or more units are required for each therapeutic administration.

As previously mentioned, the compounds of Formula I have general anthelmintic activity and accordingly a further and most important aspect of this invention provides a method of treating helminthic infections in a host animal which comprises administering, usually orally, to the animal in a sufficient nontoxic, but effective, dose an anthelmintic compound falling within the definition of Formula I, generally in the form of a pharmaceutical or veterinary composition as hereinbefore described. The daily dose range commonly used is from about 1 mg./kg. to about 300 mg./kg., preferably about 3 mg./kg.–50 mg./kg. depending on the species of host and regimen used. One dose per day administration is preferred but up to five of the dosage units described above may be used if desired. The daily dose range is therefore identical to the dosage unit range.

Where tableting is used, the resulting tablets may be then coated with methyl methacrylate to form an enteric coating, i.e., a coating which is substantially insoluble in gastric secretion but substantially soluble in intestinal fluids.

The compositions thusly prepared are administered, usually orally, to an infected or suscepticle host from 1-5 times daily for curative or prophylactic anthelmintic activity.

In addition to the activity against Nematodes as noted above, these compounds, especially the thio compounds, have activity against lungworms or Cestodes (tapeworm).

The following examples illustrate syntheses which may be employed in formulating the compositions of the invention but are not considered limiting the invention described herebefore.

EXAMPLE 1

| Typical Cattle Bolus | | |
|---|---|---|
| 5-(2-Pyridyl)-thio-2-carbomethoxy-aminobenzimidazole | 0.15 | grams |
| Calcium Phosphate | 2.5 | grams |
| Maize Starch | 0.54 | grams |
| Talcum | 0.14 | grams |
| Gum Arabic | 0.15 | grams |
| Magnesium Stearate | 0.5 | grams |

The calcium phosphate and the anthelmintic compound are thoroughly mixed, and the mixture reduced to a particle size finer than 60 mesh. About one-half of the starch is added, as an aqueous paste, and the resulting mixture granulated. The granules are passed through a No. 10 mesh screen and dried at 110°–130°C. for about 8 hours. The dried materials then passed through a No. 16 mesh screen. The guar gum and the balance of the starch are added and the mixture thoroughly blended. Finally, the remainder of the ingredients are added and the entire mass thoroughly mixed and compressed into a bolus. The magnesium stearate, talcum and gum acacia are of a particle size to pass a No. 10 mesh screen.

EXAMPLE 2

| Typical Sheep Drench | Parts by Weight |
|---|---|
| 2-(4-Pyridyloxy)-2-carbomethoxy-aminobenzimidazole | 60 |
| Terra Alba English | 35.5 |
| Tragacanth, U.S.P. | 3.0 |
| Sodium Lauryl Sulfate | 1.5 |
| Water | |

The above solid components are thoroughly mixed, giving a water dispersable powder. This powder can be directly admixed with water in concentrations on the order of 10.5 g. of powder to 5 cc. of water.

EXAMPLE 3

| Novel Sheep Drench | |
|---|---|
| 5-(4-Pyridylthio)-2-carbomethoxy-aminobenzimidazole | 2 grams |
| 0.1N HCl solution | quantum sufficient to make 1 liter |

EXAMPLE 4

A solution of 0.1 m. of potassium hydroxide in water is added to an ethanol (100 ml.)-water (175 ml.) mixture containing 15.4 g. (0.1 m.) of 3-amino-4-nitrophenol. The mixture is then heated to 50°C. at which point a solution of 0.1 m. of 4-chloropyridine in 75 ml. of ethanol is added dropwise over a 45 minute period. Then the mixture is heated at reflux for 18 hours, cooled and worked up to give a crystalline yellow solid, m.p. 170°–175°C. of 5-(4-pyridyloxy)-2-nitroaniline.

This material is suspended in ethyl acetate and hydrogenated at 65 p.s.i. with 5% Pd/C (1 g.). After the theoretical uptake of hydrogen, the filtered reaction mixture is concentrated to an oil. The oil is diluted with 300 ml. of aqueous ethanol and the pH adjusted to 5 using glacial acetic acid. 1,3-Bis-(carbomethoxy)-5-methylisothiourea (0.1 m.) is added. The mixture is heated at reflux overnight then worked up to give methyl 5-(4-pyridyloxy)-benzimidazolecarbamate, m.p. 220°–224°C.

EXAMPLE 5

Repeating the procedure of Example 4 using 2-chloropyridine gives methyl 5-(2-pyridyloxy)-benzimidazolecarbamate, m.p. 246°–253°C.

EXAMPLE 6

A mixture of 6.1 g. of pyridin-2-thiol, 7.3 g. of potassium hydroxide and 9.7 g. of 5-chloro-2-nitroacetanilide in 400 ml. of aqueous ethanol is heated at reflux overnight. The mixture is diluted with water to cloudiness. The solid which separates upon standing is collected and dried (9 g.) then hydrogenated in ethyl acetate with 1.0 g. of platinum oxide overnight. The filtered mixture is treated with activated carbon, filtered and concentrated to give a brown oil.

The oil (7.9 g.) is taken into aqueous ethanol, the pH adjusted to 5 with glacial acetic acid and 10.3 g. of 1,3-bis-(carbomethoxy)-5-methylisothiourea added. After heating at reflux overnight the desired 5-(2-pyridylthio)-benzimidazolecarbamate, m.p. 206°–209°C., is obtained.

EXAMPLE 7

A mixture of 3.7 g. of 5-(4-pyridylthio)-2-nitroaniline (m.p. 167°–170°C., prepared as in Example 6, using pyridin-4-thiol) in 150 ml. of ethanol, 3 ml. (0.035 mol.) of concentrated hydrochloric acid with 0.5 g. of 5% palladium-on-charcoal is hydrogenated at 53 lb. hydrogen pressure. The filtrate from the hydrogenation mixture is added dropwise over 45 minutes at 5°C. to a previously reacted carbomethoxycyanamide mixture [2.52 g. (0.06 mol.) of cyanamide in 5 ml. of water with 5.87 g. (0.06 mol.) of methyl chloroformate in 10 ml. of acetone at 5°–10°C. which had been neutralized with 2.4 g. of sodium hydroxide]. After reaction was complete, the volatile solvent was removed and the mixture heated 1 hour at 85°C. Water was added to separate methyl 5-(4-pyridylthio)-benzimidazolecarbamate, m.p. 230°–234°C. (dec.).

EXAMPLE 8

Repeating the procedure of Example 7 but using pyridin-3-thiol gives methyl 5-(3-pyridylthio)-benzimidazolecarbamate; using 5-chloropyridin-2-thiol gives methyl 5-(5-chloro-2-pyridylthio)-benzimidazolecarbamate; using 5-bromopyridin-2-thiol gives methyl 5-(5-bromo-2-pyridylthio)-benzimidazolecarbamate; using 5-iodopyridin-2-thiol gives methyl 5-(5-iodo-2-pyridylthio)-benzimidazolecarbamate; using 5-cyanopyridin-2-thiol gives methyl 5-(5-cyano-2-pyridylthio)-benzimidazolecarbamate; using 3-methylpyridin-4-thiol gives methyl 5-(3-methyl-4-pyridylthio)-benzimidazolecarbamate; using 2,6-dimethylpyridin-4-thiol gives methyl 5-(2,6-dimethyl-4-pyridylthio)-benzimidazolecarbamate; using 5-ethylpyridin-2-ethyl mercaptan gives methyl 5-(5-ethyl-2-pyridylthioethyl)-benzimidazolecarbamate; using pyridin-2-ethyl mercaptan gives methyl 5-(2-pyridylthioethyl)-benzimidazolecarbamate; using pyrimidin-4-thiol gives methyl 5-(4-pyrimidylthio)-benzimidazolecarbamate; using 4-mercaptothiazole gives methyl 5-(4-thiazolylthio)-benzimidazolecarbamate; using 2-mercaptothiazole gives methyl 5-(2-thiazolylthio)-benzimidazolecarbamate; using 1-methyl-2-mercaptoimidazole gives methyl 5-(1-methylimidazolyl-2-thio)-benzimidazolecarbamate; using 2-mercaptoimidazole gives methyl 5-(2-imidazolylthio)-benzimidazolecarbamate; using 2-mercaptothiophene gives methyl 5-(2-thienylthio)-benzimidazolecarbamate; using 2-mercapto-1,3,4-thiadiazole gives methyl 5-[2-(1,3,4-thiadiazolyl)-thio]-benzimidazolecarbamate; using 2-mercapto-1,2,4-thiadiazole gives methyl 5-[2-(1,2,4-thiadiazolyl)-thiol]-benzimidazolecarbamate; using 2-mercapto-1,3,4-oxadiazole gives methyl 5-[2-(1,3,4-oxadiazolyl)-thio]-benzimidazolecarbamate; using 5-mercaptooxazole gives methyl 5-(5-oxazolylthio)-benzimidazolecarbamate; using 5-mercaptotetrazole gives methyl 5-(5-tetrazolylthio)-benzimidazolecarbamate; using 5-mercapto-1-methyltetrazole gives methyl 5-(1-methyl-5-tetrazolylthio)-benzimidazolecarbamate; using 5-mercapto-1,2,4-triazole gives 5-[5-(1,2,4-triazolyl)-thio]-benzimidazolecarbamate; using pyrazin-2-thiol gives methyl 5-(2-pyrazinylthio)-benzimidazolecarbamate. Other mercaptan starting materials are disclosed in U.S. Pat. No. 3,516,997.

EXAMPLE 9

Following the method of Example 4 and the cyanamide condensation, but using 2-chloromethyl-6-methylpyridine gives methyl 5-(6-methyl-2-pyridylmethyloxy)-benzimidazolecarbamate; using 5-α-chloroethyl-2-methylpyridine gives methyl 5-(2-methyl-5-pyridyl(α)ethyloxy)-benzimidazolecarbamate; using 2-chloro-5-chloromethylthiophene gives methyl 5-(2-chloro-5-thienylmethyloxy)-benzimidazolecarbamate; using 3-bromomethylthiophene gives methyl 5-)3-thienylmethyloxy)-benzimidazolecarbamate; using 2-chloromethylfurane gives methyl 5-(2-furylmethyloxy)-benzimidazolecarbamate; using 2-isobutyl-5-chloromethylthiophene gives methyl 5-(2-isobutyl-5-thienylmethyloxy)-benzimidazolecarbamate; using 6-chloromethylpyrimidine-2,4-dione gives methyl 5-(6-pyrimidin-2,4-dioxy-methyloxy)-benzimidazolecarbamate; using 4-chloromethyl-3-methylisoxazole gives methyl 5-(3-methyl-4-isoxazolylmethyloxy)-benzimidazolecarbamate. Using the corresponding mercaptans in the above reaction gives the preferred thio congeners.

EXAMPLE 10

A slurry containing the desired benzimidazolecarbamate and ethanol-water (50:50) is acidified with concentrated hydrochloric acid. Dilution with ethyl ether separates the desired hydrochloride salt from the mixture. An ethanol slurry of 500 mg. of methyl 5-(4-pyridylthio)-benzimidazolecarbamate is treated with a few drops of dilute sulfuric acid and the resulting solution diluted with ethyl ether to separate the sulfate salt.

We claim:
1. A chemical compound of the structure:

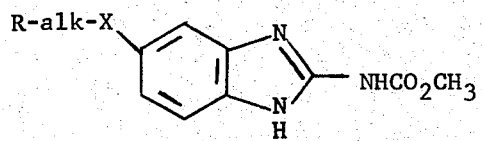

in which R is furyl or thienyl; and X is thio or oxy, said furyl or thienyl being C-attached to X through alk which is an alkylene chain of from 1–4 members.

2. A compound of claim 1 in which X is thio.
3. A compound of claim 2 in which R is thienylmethyl.
4. A compound of claim 2 in which R is furylmethyl.
5. A compound of claim 1 in which R is attached to X by a methylene group.
6. The method of producing anthelmintic activity in host animals susceptible to helminthic infections comprising administering orally to said animals an anthelmintically effective but nontoxic quantity of a compound of claim 1.
7. The method of producing anthelmintic activity in host animals susceptible to helminthic infection comprising administering orally to said animals an anthelmintically effective but nontoxic quantity of the compound of claim 2.
8. The method of producing anthelmintic activity in host animals susceptible to helminthic infection comprising administering orally to said animals an anthelmintically effective but nontoxic quantity of the compound of claim 5.
9. An anthelmintic composition comprising a carrier and an anthelmintically effective but nontoxic quantity of a compound of claim 1, said quantity being from about 1–100 mg./kg. per dosage unit.
10. An anthelmintic composition comprising a carrier and an anthelmintically effective but nontoxic quantity of the compound of claim 2, said quantity being from about 1–100 mg./kg. per dosage unit.
11. An anthelmintic composition comprising a carrier and an anthelmintically effective but nontoxic quantity of the compound of claim 5, said quantity being from about 1–100 mg./kg. per dosage unit.

* * * * *